United States Patent [19]

Saper

[11] Patent Number: 4,994,018
[45] Date of Patent: Feb. 19, 1991

[54] INTRA-AORTIC BALLOON ASSEMBLY

[75] Inventor: Lawrence Saper, New York, N.Y.

[73] Assignee: Datascope Corporation, Oakland, N.J.

[21] Appl. No.: 359,643

[22] Filed: May 31, 1989

[51] Int. Cl.$^5$ .............................................. A61N 1/362
[52] U.S. Cl. ...................................... 600/18; 128/772; 604/96
[58] Field of Search .................... 600/18; 128/772; 604/96, 97, 98, 99

[56] References Cited

U.S. PATENT DOCUMENTS

| | | | |
|---|---|---|---|
| 4,290,428 | 9/1981 | Durand et al. | 128/349 B |
| 4,362,150 | 12/1982 | Lombardi, Jr. et al. | 128/1 D |
| 4,413,989 | 11/1983 | Schjeldahl et al. | 604/96 |
| 4,467,790 | 8/1984 | Schiff | 128/1 D |
| 4,531,512 | 7/1985 | Wolvek et al. | 128/1 D |
| 4,540,404 | 9/1985 | Wolvek | 604/96 |
| 4,545,390 | 10/1985 | Leary | 128/772 |
| 4,616,652 | 10/1986 | Simpson | 128/344 |
| 4,616,653 | 10/1986 | Samson et al. | 128/344 |
| 4,641,654 | 1/1987 | Samson et al. | 128/344 |
| 4,664,113 | 5/1987 | Frisbie et al. | 128/344 |
| 4,723,936 | 2/1988 | Buchbinder et al. | 604/95 |
| 4,739,768 | 4/1988 | Engelson | 128/658 |

FOREIGN PATENT DOCUMENTS 8600010  6/1984  PCT Int'l Appl. .................. 600/18

Primary Examiner—Lee S. Cohen
Assistant Examiner—Scott M. Getzow
Attorney, Agent, or Firm—Darby & Darby

[57] ABSTRACT

A dual tubular member intra-aortic balloon assembly (1) has an inflatable balloon (4) bonded, at its proximal end, to an outer tubular member (2), and at its distal end, to an inner tubular member (3). The inner tubular member is composed of metal, being axially rigid yet bendable along its length. A flexible forwardly projecting extension (12) is attached to the inner tubular member for guiding the relatively stiff balloon assembly over a guide wire (9) through a tortuous arterial path, without causing buckling or misplacement of the guide wire. The junction between the inner tubular member and the flexible tubular member extension is embedded within a flexible tip (10) which reinforces the juncture to prevent balloon failure due to bending stress at the same time, enables a tighter balloon wrapping by eliminating the enlarged junction of the inner tubular member and flexible tip within the balloon membrane.

8 Claims, 1 Drawing Sheet

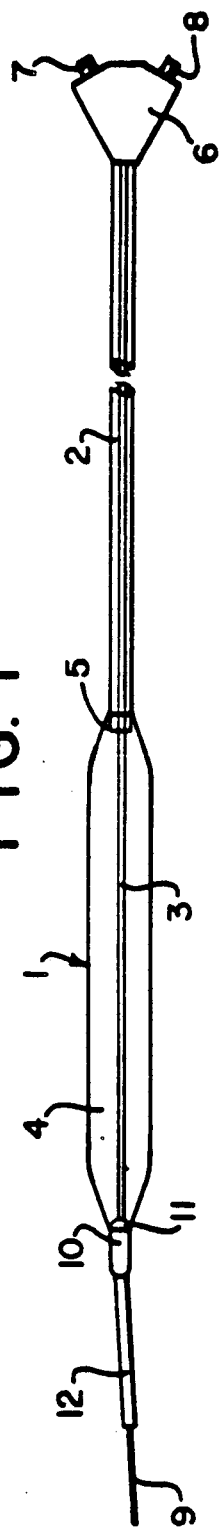
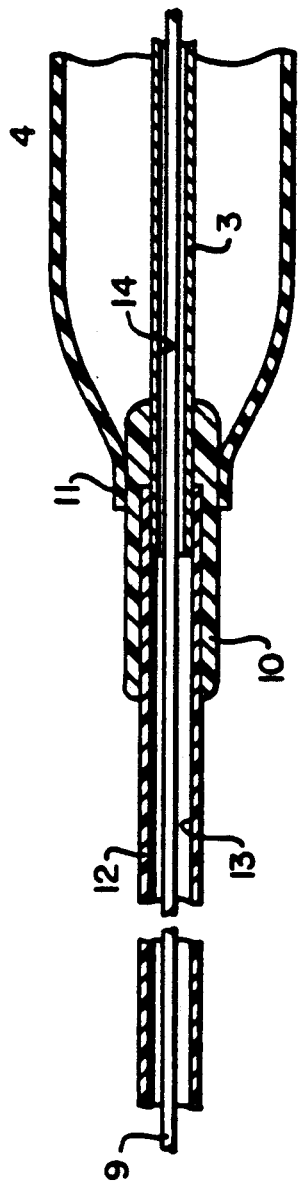
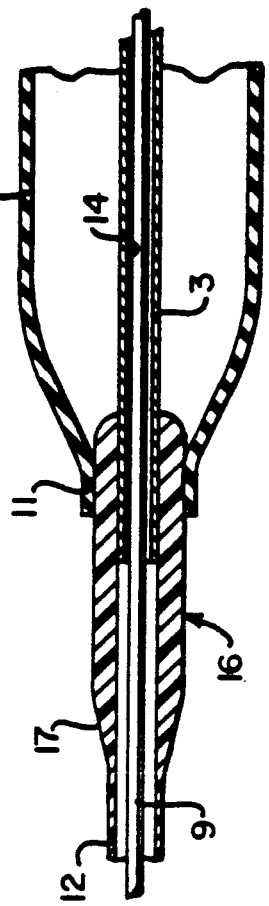
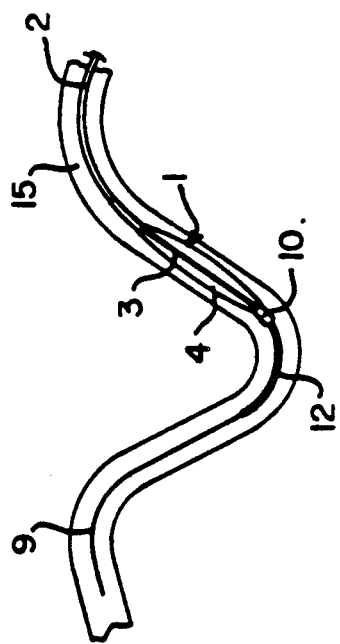

INTRA-AORTIC BALLOON ASSEMBLY

TECHNICAL FIELD

This invention relates to intra-aortic balloon assemblies designed for enhanced guidability through tortuous arteries.

BACKGROUND OF THE INVENTION

Intra-aortic balloons are designed to assist a failing heart through cyclic inflation/deflation in the descending thoracic aorta, in counterpulsation to the heart. Such balloons are generally inserted percutaneously into the femoral artery and advanced along the arterial path to the descending thoracic aorta. Intra-aortic balloons consisting of a catheter with two coaxial tubular members defining two lumens, are known, for example, as shown in U.S. Pat. No. 4,540,404 to Wolvek. An outer tubular member (outer lumen) is included, being substantially circumferentially rigid but longitudinally flexible, having its distal end attached to the proximal end of an inflatable balloon. An inner tubular member (inner lumen) is coaxially disposed in the outer tubular member, and is similarly longitudinally flexible, having its distal end attached to the balloon distal end. The inner tubular member supports the balloon.

The intra-aortic balloon is wrapped around the inner tubular member for insertion into the artery, with vacuum applied to the balloon interior to assure tight wrapping and the absence of air pockets. Tight, smooth wrapping is essential as a small diameter and smooth balloon outer surface provide less resistance during insertion, and reduce arterial wall contact during travel through the artery.

Intra-aortic balloon assemblies of this type usually utilize a guide wire which is inserted through an incision into the common femoral artery, such as by using the standard Seldinger technique. The guide wire is thin and readily guidable through the artery. Once the wire is positioned, the inner tubular member of the balloon assembly is passed over the wire until the balloon reaches the desired location. The balloon is then unwrapped, connected to its pumping apparatus and counterpulsation initiated.

While a guide wire can be directed through delicate, tortuous and narrow vasculature, it is often difficult to advance the balloon assembly over the guide wire for any great distance. If the inner tubular member is relatively rigid in its longitudinal duration, it may not track properly over the wire because advancement of the assembly will buckle the wire in a narrow turn, pulling the guide wire out of the distal vessel and posing a possible risk of penetration of the vessel wall by the relatively rigid member. On the other hand, catheters having a soft, longitudinally flexible inner tubular member, such as that disclosed in U.S. Pat. No. 4,402,307, have no difficulty in following the wire. However, some practitioners may prefer the stiff feel provided by a rigid inner lumen.

One arrangement for providing better guidability to a relatively rigid balloon catheter is shown in U.S. Pat. No. 4,362,150 to Lombardi, Jr. et al.. A metallic inner tubular member is used which does not extend for the entire length of the balloon, with the member being bendable but relatively rigid in its axial direction. The balloon distal end is fixed to an inwardly projecting segment of a longitudinally flexible outer tubular member. The metallic inner tubular member is coaxial with the flexible tubing within the balloon membrane. This provides some flexibility to the forward part of the balloon. However, since the flexible tubing extends into the balloon membrane, it is only marginally effective in providing sufficient flexibility for balloon guidance. Also, insertion and travel of the balloon along a tortuous path concentrates bending stresses at the flexible tube/rigid tube juncture within the balloon, which may weaken the juncture, causing separation and balloon failure. In addition, the enlarged cross-section of the tube juncture within the balloon membrane retards the tightness of the wrap, and creates a larger wrapped diameter, limiting the ease of insertion of the assembly into the femoral artery.

In U.S. Pat. No. 4,739,768 to Engelson, a noncoaxial, single lumen catheter for use with a guide wire is disclosed which includes a relatively stiff proximal segment and a relatively flexible distal segment. The tubular member has a flexible distal extension for leading the relatively stiff inner tubular member along a tortuous path. However, the catheter of Engelson is not a balloon catheter, rather being designed to deliver fluids to a particular target site.

SUMMARY OF THE INVENTION

It is an object of the present invention to provide an intra-aortic balloon assembly which has a relatively stiff metallic inner tubular member yet has the guidability of an assembly with a flexible inner tubular member.

Another object is to provide a dual tubular member intra-aortic balloon assembly, including a metallic inner tubular member of longitudinally stiff but bendable metal, and having a leading flexible portion for easing the assembly through a tortuous path.

Another object is to provide a dual lumen intra-aortic balloon assembly which has a flexible distal extension attached to a bendable metallic inner tubular member at the distal end of the balloon, so that the junction will not reside within the balloon membrane.

According to the present invention, a dual tubular member intra-aortic balloon assembly includes a flexible outer tubular member, and a metallic inner tubular member which is relatively stiff in the axial direction but is bendable. The metallic inner tubular member extends through the balloon for its entire length. The assembly has a flexible inner tubular member extension, which extends forwardly from the balloon distal end for a distance sufficient to lead the relatively longitudinally stiff balloon assembly over a guide wire to a desired location without buckling or inadvertent wire withdrawal. That is, the flexible extension can easily bend and follow a tortuous path over the guide wire through the artery. A tip member encapsulates the juncture between the flexible extension and the metallic inner tubular member, reinforcing the juncture to prevent separation due to bending stress, without impeding the ability of the balloon membrane to be compactly wrapped about the inner lumen.

DESCRIPTION OF THE DRAWINGS

Other objects and advantages of the present invention will become more apparent upon reference to the following specification and annexed drawings in which:

FIG. 1 is an elevation view of the intra-aortic balloon assembly of the present invention;

FIG. 2 is an enlarged cross-sectional view of the tip of the intra-aortic balloon of FIG. 1;

FIG. 3 is an illustrative view of the intra-aortic balloon of the present invention traveling along a tortuous arterial path; and FIG. 4 is an alternative embodiment of the intra-aortic balloon assembly of the present invention.

DETAILED DESCRIPTION OF THE INVENTION

Referring to FIG. 1, a dual lumen intra-aortic balloon assembly 1 is shown, having an outer tubular member 2 and a coaxial inner tubular member 3. The outer tubular member 2 is of a suitable plastic material, such as polyurethane. An expandable membrane is used as a balloon 4 having its proximal end 5 sealed in an airtight manner to the outer surface of the distal end of the outer tubular member 2. The balloon 4 is of a nonthrombongenic material, which is inflatable but substantially non-distensible.

A Y-type fitting 6 is provided which has access ports 7 and 8. A proximal end of the outer tubular member 2 is in communication with the fitting at port 7 so that the balloon 4 can be inflated and deflated by suitable apparatus (not shown) which is connectable to the port.

The inner tubular member 3 is preferably made of metal such as stainless steel. The dimensions of the inner tubular member 3 are typically, for example about 0.046 inch outer diameter, with a wall thickness of about 0.005 inch. This permits the inner tubular member to have some flexibility, i.e. it can be bent as it is passed through the artery. However it is relatively rigid in the axial direction.

The proximal end of the inner tubular member 3 is coupled to the access port 8 of fitting 6. A guide wire 9 can thus be advanced through the inner tubular member, and through the artery, for guiding the balloon assembly to the desired site. The metallic inner tubular member 3 extends through the length of the balloon 4, terminating in a tip 10 (see FIG. 2). A distal end 11 of the balloon is attached to the tip 10 with a gas-tight seal.

Referring to FIG. 2, a flexible inner tubular member extension 12 is attached, in a fluid-tight manner, to the inner tubular member 3 within the tip 10. The distal end of the inner tubular member is within the proximal end of the extension. The extension 12 extends forwardly from the tip 10 and balloon distal end. The hollow metal inner tubular member 3, and extension 12 may be fixed, for example, by insert molding or adhesive bonding. Similarly, the balloon distal end may be adhesively bonded to the tip. The extension 12 is preferably composed of a soft plastic material such as polyurethane. The extension precedes the tip by from 2 to 8 cm, preferably from 4 to 6 cm. The flexible inner tubular member extension 12 has a bore 13, for passage of the guide wire 9 therethrough.

Embedding the junction of the flexible tubular member extension and the stiff inner tubular member within the tip 10, rather than joining within the balloon membrane, assures that no bending stresses are concentrated within the balloon. Instead, the stresses are concentrated in the tip, which provides additional reinforcement to prevent separation of the extension and tubular member from each other. In addition, embedding the juncture within the tip obviates an enlarged junction within the balloon, making possible a tighter balloon wrap.

The guide wire 9 extends through a bore 14 of the rigid inner tubular member 3 and through the bore 13 of the flexible inner tubular member extension 12. The guide wire 9 has a relatively small diameter, typically about 0.035 to 0.038 inch. The bore 14 is of sufficient diameter to permit easy passage of the guide wire therethrough. The bore 13 of the flexible extension may be of somewhat larger diameter, to accommodate the inner member distal end therein.

To prepare the balloon for insertion, the balloon membrane is compactly wrapped about the portion of the inner tubular member 3 which is disposed within the balloon membrane. Thus, the inner tubular member supports the balloon during wrapping and during travel through the artery.

Referring to FIG. 3, the balloon assembly 1 is shown traveling over the guide wire 9, already inserted in a curved artery 15. The flexible extension 12 precedes the balloon 4 (shown unwrapped for ease in illustration) and the metallic inner tubular member 3. Being flexible, the extension 12 can follow the curved path, providing additional support for the guide wire to prevent buckling. The trailing part of the assembly, with the stiffer but bendable metallic inner tubular member, can therefore safely follow the flexible extension 12 into and through the turns of the artery. As the assembly travels through the artery, the tip 10 protects the juncture between the extension and the inner tubular member, while assisting forward travel by leading the balloon through the curve.

FIG. 4 shows another embodiment of the invention, having a flexible tubular member extension/tip 16 of unitary construction. This avoids a separate step in manufacture, bonding of the tip to the extension. The extension/tip 16 may be produced by molding a soft and flexible plastic. With such a construction, the proximal end of the tip is preferably tapered at 17 to further facilitate passage of the tip through the artery. Similar to the previous embodiment, the inner tubular member 3 is inserted and fixed to the tip 18, such as by insert molding or adhesive bonding. Such a unitary tip design is easy to produce, reducing costs while simplifying balloon assembly.

While this invention is described in relation to particular embodiments of an intra-aortic balloon for assisting in counterpulsation of a heart, it will be understood that other equivalent embodiments will be apparent to those skilled in the art which are within the scope of the present invention.

What is claimed is:

1. A dual tubular member intra-aortic balloon assembly for insertion into a vessel comprising:
   an outer tubular member;
   an inner tubular member having a distal end coaxial with the outer tubular member;
   a balloon membrane having a proximal end attached to a distal end of the outer tubular member, and a distal end attached to the inner tubular member, the inner tubular member being axially rigid but bendable for at least that portion within the balloon membrane;
   a flexible inner tubular member extension attached to the inner tubular member distal end and extending forwardly in an amount sufficient for guiding the intra-aortic balloon assembly through the vessel;
   a tip disposed at said distal end of the balloon membrane, the junction of the inner tubular member and the flexible inner tubular member extension embedded therein.

2. The intra-aortic balloon assembly of claim 1 wherein the tip and flexible inner tubular member extension are of unitary construction.

3. The intra-aortic balloon assembly of claim 1 wherein said tip is flexible.

4. The intra-aortic balloon assembly of claim 1 wherein the flexible tubular member extension extends from about 0.5 to 8 cm from a distal end of the tip.

5. The intra-aortic balloon assembly of claim 4 wherein the flexible tubular member extension extends from about 2 to 6 cm from the distal end of the tip.

6. The intra-aortic balloon assembly of claim 1 wherein a distal end of the tip has a rounded shape.

7. The intra-aortic balloon assembly of claim 1 wherein the tip is tapered from a distal end to a proximal end.

8. The intra-aortic balloon assembly of claim 1 wherein said inner tubular member is made of metal.

* * * * *